United States Patent [19]

MacDonald

[11] Patent Number: 4,576,936

[45] Date of Patent: Mar. 18, 1986

[54] 6α-FLUORO-9α-CHLORO-PREDNISOLONE 17,21-DIESTERS

[75] Inventor: Peter MacDonald, Arese, Italy

[73] Assignee: Sterosynt Ltd., Bristol, Great Britain

[21] Appl. No.: 361,119

[22] Filed: Mar. 23, 1982

Related U.S. Application Data

[63] Continuation of Ser. No. 207,807, Nov. 17, 1980, abandoned.

[30] Foreign Application Priority Data

Nov. 16, 1979 [IT] Italy .......................................... 27353
Oct. 9, 1980 [IT] Italy .......................................... 49853

[51] Int. Cl.$^4$ ............................................. A61K 31/56
[52] U.S. Cl. ................................. 514/180; 260/397.45
[58] Field of Search ................... 260/397.45; 424/238, 424/243

[56] References Cited

U.S. PATENT DOCUMENTS 3,980,778 9/1976 Ayer et al. .......................... 424/243
4,024,131 3/1977 Villax ............................. 260/397.45
4,261,984 4/1981 Alvarez ............................... 424/238

Primary Examiner—Elbert L. Roberts
Attorney, Agent, or Firm—Bucknam and Archer

[57] ABSTRACT

Novel 6α-fluoro-9α-chloro-16β-methyl-prednisolone 17, 21-diesters, and a method for their preparation, are described. The novel products are particularly valuable as anti-inflammatory agents.

1 Claim, No Drawings

6α-FLUORO-9α-CHLORO-PREDNISOLONE 17,21-DIESTERS

This is a continuation of application Ser. No. 207,807, filed Nov. 17, 1980, now abandoned.

BACKGROUND OF THE INVENTION AND PRIOR ART

During the 1950's and 1960's many pharmaceutical concerns launched extensive programs to synthesize modified corticosteroids. The objective was to create systemically active compounds having more potent antiflammatory activity than the naturally occuring corticoids but without correspondingly elevated levels of side effects such as interference with the pituitary-adrenal relationship (leading to adrenal insufficiency) and effects on electrolyte balance and glucose metabolism.

The initial efforts resulted in certain quite potent compounds of the prednisolone series having a 9αfluoro constituent in combination with 16-methyl or 16αhydroxy substitution, such as Betamethasone, dexamethasone, and triamcinolone. Certain compounds having 16α-methyl substitution along with a 6αfluoro constituent (paramethasone) or with combined 6α, 9αfluoro substitution (flumethasone) also proved interesting.

In all these compounds the problem of electrolyte imbalance (primarily sodium retention with potassium depletion) was substantially reduced. Various theories were advanced for this, with one or more groups being said to enhance potency ($\Delta'$ and 9αF) with (9αF) or without ($\Delta'$) some degree of potentiation of mineralcorticoid activity and with other substituents (16-OH, αCH$_3$ or βCH$_3$) being said to attenuate somewhat the mineralcorticoid effect. In any event, when the lower doses made possible by enhanced potency were used, observed electrolyte activity was reduced and it is generally accepted today that at therapeutic doses the compounds which are $\Delta'^4$ dienes with 6' and/or 9α halogen substitution combined with 16- methyl or 16αhydroxy substitution do not cause an unacceptable degree of electrolyte imbalance.

Despite these early successes, significant separation of other side effects from therapeutic activity proved difficult, although it was later noted that in some cases the 16αmethyl substitution did by itself augment anti-inflammatory activity somewhat more than glycogen deposition and that the 16βmethyl substitution diminished glycogenic properties somewhat without altering the anti-inflammatory activity. Thus, these compounds are still widely used today in various forms: Tablets and syrups for normal systemic application (Betamethasone, Dexamethasone, and Triamcinolone), suspensions for long acting systemic or parenteral applications (Betamethasone acetate, Paramethasone acetate and Triamcinolone diacetate), and creams or aerosols for topical application (Betamethasone and Dexamethasone)

In the mid-1960's, attention turned to attempts at development of highly effective topical corticoids with little or no systemic effects. The former objective was pursued through a combination of potentiated anti-inflammatory activity per se and/or improved absorption through the stratum corneum. The latter objective was pursued through reduction of systemic activity per se and/or reduction in the ability to migrate from the epidermis into the dermis after penetration of the stratum corneum.

The two primary corticoids developed at that time which are still major factors today are the 16–17 acetonides of Triamcinolone and its 6α, 9α diflorocounterpart, fluocinolone. For some reason, still not fully understood, tramcinolone acetonide is about ten times as active as triamcinolone topically, but only equiactive systemically. Flucinolone acetonide is essentially ineffective systemically even though it is perhaps even more active topically than its triamcinolone counterpart. For topical steroids these compounds plus related Fluandrenalone (6αF, 16αOH, hydrocortisone 17,21 acetonide) today represent more than one half of all prescriptions in the United States.

At the end of the 1960's, much attention was given to the esters of the above discussed compounds and of other compounds, such as beclomethasone (the resulting dipropionate), which had not found earlier commerical use. In some, but by no means all instances, the esterification at 17 and/or 21 was found to improve the potency of therapeutic effect as evaluated by Vasoconstriction assays. What is most striking from the literature of that time is the unpredictability of the results of esterification when trying to apply knowledge gained with one skeletal series to another skeletal series. Mostly this is due to the subtle alteration of the shapes of molecules caused by even minor structural differences and it is on the basis of shape that hormones are recognized by their receptors.

One of the most completely explored series of esters is those of Betamethasone (9αF, 16β-CH$_3$). When esterified in the 17 position, betamethasone is potentiated from activity of 1% of fluocinalone acetonide to up to 350% of fluocinolone acetonide as the ester chain increases from acetate through butyrate and propionate up to valerate, the latter compound being one of the most widely used topical anti-inflammatory agents today. The 17-benzoate, U.S. Pat. No. 3,529,060, has recently been found to be of equal activity to the valerate. Esterification in the 21-position also causes some potentiation of anti-inflammatory activity, but primarily imparts more long acting effects as was expected, from early findings, mentioned previously, on the 21-acetates of betamethasone. The esters of Betamethasone today represent almost one-third of prescriptions for topical steroids in the United States.

Another series receiving a lot of attention were the 6,9 difluoroprednisolones through the work of Gardi, et al described for example in the Journal of Medicinal Chemistry, 15, 556 (1972) and 15,783 (1972), in Steroids, 16:6, 663 (1970), and in U.S. Pat. Nos. 3,780,177 (6,9 difluoroprednisolone 17-butyrale, 21-acylates), 3,784,692 (the corresponding 17 propionates, 21 acylates), 3,691,214 (17-valerates) and 3,857,941 (17-benzoates). Commercial uses of these compounds has not yet begun in the United States.

Finally, the diacetate of 6,9 difluoro-16methyl-prednisolone was discovered by Upjohn to be a very interesting compound-one subsequently commercialized in the United States. However, none of the other esters appear to have received attention.

An excellent summary of the history of structural modifications of corticosteroids appears as Chapter 9, Anti-inflammatory Steroids, in Anti-Inflammatory Agents, Scheerer (Ed), Academic Press (1974).

Despite the work over a decade ago with the 6,9 difluoroprednisolones esters, the 6,9 difluoro 16 methyl prednisolone, 17,21 diacetate and despite the even earlier work with the betamethasone (9αfluoro, 16β-CH₃ prednisolone) esters and the Beclomethasone (9α-chloro, 16β-CH₃ prednisolone) esters, surprisingly the only literature reference describing the 9αCl, 6αF 16 methylated prednisolone or its esters appears to be the mention of 16βmethyl diacetate as an intermediate in Belgian Pat. No. 858709 (1978) for the production of certain 9,11 halogenated steroids.

I have now discovered that while the 16αmethyl series produce unacceptable impact on the adrenal and thymus, the 16βmethyl series are important anti-inflammatory agents in the cotton pellet granuloma rat assay and the modified McKensie vasoconstriction assay in man, and are exhibiting only limited effect on the thymus and adrenal glands.

DETAILED DESCRIPTION OF THE INVENTION

The invention relates to novel 6α-fluoro-9α-chloro-prednisolone 17,21-diesters having the general formula I

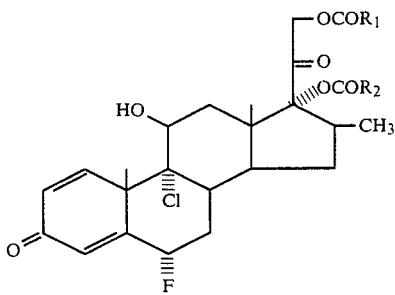

in which $R_1$ and $R_2$ are alkyl groups containing 1-6 carbon atoms or aryl groups.

The compounds of formula I are prepared using known methods from the 6α-fluoro-9β,11β-epoxy-pregna-1,4-dienes having the general formula II

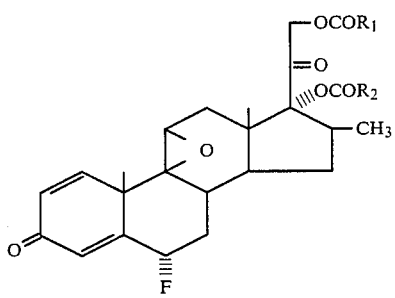

where $R_1, R_2$ have the meanings given above.

In our Italian application No. 25149 A/79 there is described a novel and general method for the preparation of the compounds of Formula II from the corresponding 3-acetoxy-9β, 11β-epoxy-pregna-1,3, 5-trienes of general formula III

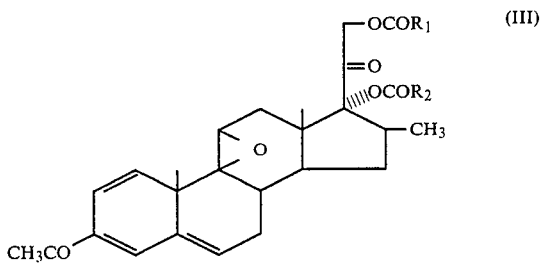

where $R_1, R_2$ have the meanings given above. In our Italian application 26227 A/79 there is described an alternative method for the preparation of 6α-fluoro-9β,11β-epoxy-pregna-1,4-dienes having the general formula II from the corresponding 1,2-dihydrocompounds having the general formula IV,

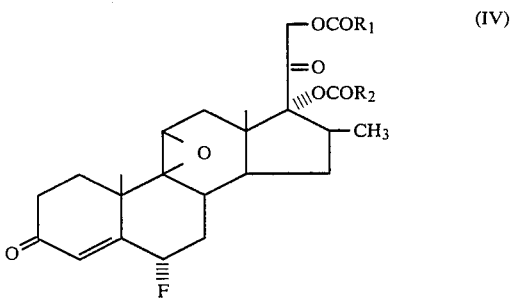

where $R_1, R_2$ have the meanings given above.

In the above-mentioned applications there is also described the conversion of certain compounds of general formula II, into known corticoids such as diflorasone diacetate, and 6α,9α-difluoroprednisolone 17,21-diacetate through reaction with hydrogen fluoride.

The reaction of the compounds of formula II with hydrogen chloride is carried out under any of the conditions usual for the chlorination of epoxy steroids. For example the epoxide, optionally dissolved in a suitable solvent, is treated with anhydrous hydrogen chloride, aqueous hydrochloric acid, or a mixture of lithium chloride and glacial acetic acid. The preferred method of chlorination is to add the solid epoxide to a solution of lithium chloride (at least 2 moles/mole of epoxide) in glacial acetic acid.

Although the preferred method for preparing the compounds of general formula I is from the corresponding 9β,11β-epoxide of general formula II, in certain cases other methods may be conveniently used. Thus, the novel 6α-fluoro-9α-chloro-prednisolone 17,21-diesters of formula I may be obtained from the corresponding 6α-fluoro-9α-chloro-prednisolones by conversion to a 1% 21-alkylorthoalkanoate ester by known procedures, followed by cleavage thereof with acid using known techniques to give the corresponding 17-alkanoate ester, followed by acylation in position 21 using standard procedures.

Another method for the preparation of the compounds of general formula I which may occasionally be convenient is by dehydrogenation of the corresponding 1,2-dihydro compounds having the general formula V,

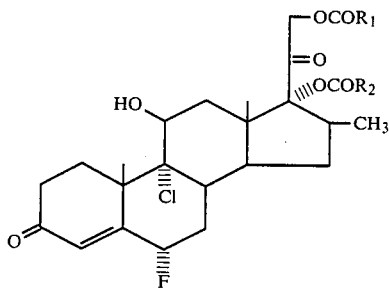

(V)

where $R_1, R_2$, have the meanings given above, using either chemical or microbiological methods. The preparation of the compounds having the formula V from the corresponding compounds of formula IV is described in our Italian application 26227 A/79. However it has been found that the dehydrogenation of the compounds of general formula V with dichlorodicyanobenzoquinone (which is the preferred chemical agent for dehydrogenation) shows rather low yields (70–80%); while the same method of dehydrogenation, applied to the compounds of general formula IV, gives 1,4-dienes of formula II in high yields (90–95%). Thus the preferred route from compound IV to compound I is usually via compound II rather than via compound V.

Preferred compounds of formula I include: the 21-acetate, 21-propionate, 21-butyrate, 21-isobutyrate, and the 21-valerate ester derivatives of 6α-fluoro-9α-chloro-16β-methyl-prednisolone 17-acetate 6α-fluoro-9α-chloro-16β-methyl-prednisolone 17-propionate 6α-fluoro-9α-chloro-16β-methyl-prednisolone 17-butyrate 6α-fluoro-9α-chloro-16β-methyl-prednisolone 17-valerate 6α-fluoro-9α-chloro-16β-methyl-prednisolone 17-benzoate Of the foregoing compounds particularly valuable are the following ones (indicated with a reference number):

(121) 6α-fluoro-9α-chloro-16β-methyl-prednisolone 17,21-diacetate (122) 6α-fluoro-9α-chloro-16β-methyl-prednisolone 17,21-dipropionate (123) 6α-fluoro-9α-chloro-16β-methyl-prednisolone 17-valerate 21-acetate (124) 6α-fluoro-9α-chloro-16β-methyl-prednisolone 17-benzoate 21-acetate (133) 6αfluoro-9αchloro-16β-methyl-prednisolone 17-propionate 21-acetate The present invention includes within its scope the method of treating an inflammatory condition in a warm-blooded animal responsive to treatment with anti-inflammatory agents which comprises administering to said animal a non-toxic, anti-inflammatory effective amount of a 6α-fluoro-9α-chloro-prednisolone 17,21-diester of formula I. The preferred compounds of formula I are valuable anti-inflammatory agents when administered topically, or locally, since they have high anti-inflammatory action as well as low glucocorticoid action on topical administration, and moreover have low glucocorticoid activity when administered systemically. The compounds thus have the desirable high anti-inflammatory action on topical application with little risk of disturbance of the mineral balance or other systemic action should the compound be absorbed.

The 6α-fluoro-9α-chloro-prednisolone 17,21-diesters of formula I may be applied topically or locally in any of the conventional pharmaceutical forms, including ointments, lotions, creams, sprays, powders, drops, (ear drops or eye drops), suppositories, tablets, pellets, or aerosols.

BIOLOGICAL ACTIVITY

The biological activity of the compounds of the invention was compared to that of beclomethasone dipropionate using the cotton pellet granuloma assay. Female rats (Sprague-Dawley) weighing about 135 g were used and into each animal, under ether anaesthesia, was implanted subcutaneously a cotton pellet weighing 10 mg. The cotton pellets were previously soaked with 25 ml of a solution of the test substance and with 50 ml of a 2% carrageen suspension and left to dry. The cotton pellets contained 0.1, 1, or 10 mcg of the test substance (ten animals were used for each concentration of each substance).

After seven days the animals were sacrificed and the granulomas that had formed around the cotton pellets were removed, dried at 80° and weighed. The adrenal and thymus glands were also removed and weighed. A similar procedure was carried out using beclomethasone dipropionate, as well as a control. The results are summarized in Table 1, with the corresponding reference numbers. It is seen from these results that the compounds cause up to 48% inhibition of granuloma formation at dosages of 1.0 mcg/rat whereas beclomethasone dipropionate was only modestly active at this low dosge. The more active compounds have an activity comparable with 10-fold dosages of beclomethasone dipropionate. Notwithstanding this elevated anti-inflammatory potency the compounds of the invention usually had no significant effects on the weights of the thymus and adrenal glands even at levels 10 times greater than the effective anti-inflammatory dosages.

TABLE 1

| Compound | Dose (mcg/rat) | % variation with respect to the controls | | |
|---|---|---|---|---|
| | | cotton pellet | adrenal gland | thymus gland |
| "121" | 0.1 | +2.5 | +7.1 | −1.2 |
| | 1 | −5.3 | +3.3 | −1.2 |
| | 10 | −42.4 | +3.7 | −2.5 |
| "122" | 0.1 | −10.6 | +3.0 | −2.0 |
| | 1 | −37.6 | +4.9 | −2.0 |
| | 10 | −63.3 | +3.0 | −6.2 |
| "123" | 0.1 | −1.4 | +1.2 | −2.4 |
| | 1 | −12.4 | +3.3 | +1.3 |
| | 10 | −52.2 | 0 | −4.2 |
| "124" | 0.1 | −11.9 | +2.2 | +0.9 |
| | 1 | −48.2 | −0.2 | +0.4 |
| | 10 | −71.1 | −2.8 | −3.2 |
| "133" | 0.1 | −1.4 | +1.6 | −5.4 |
| | 1 | −4.1 | +1.4 | −7.7 |
| | 10 | −38.5 | −3.4 | −10.0 |
| BECLO-METHASONE DIPROPIONATE | 0.1 | −0.6 | −1.4 | −3.3 |
| | 1 | −12.7 | +0.1 | −0.5 |
| | 10 | −55.0 | −1.7 | −4.7 |

The direct applicability of the anti-inflammatory activity to man is tested using the modified McKenzie/-Slaughton procedure on thirty human volunteers. Various concentrations of the compounds to be tested are prepared in alcoholic solution and placed under occulusion on intact skin of the forearms of the subjects. After 18 hours the covering is removed and the skin surfaces examined for the intense blanching indications of vasoconstriction. The examination is performed by three independent observers who scored the degree of blanching from zero to three based on blanching within each subject. Thus the maximum score is 90.

To confirm the observations of the cotton pellet granuloma rat assay, one of the compounds of this invention was so tested as were several reference anti-inflammatory compounds in routine clinical use today. The results are shown on Table 1A.

TABLE 1A

| Compound | Concentration gm/ml | Score as % of maximum |
|---|---|---|
| "122" (6α F,9α Cl- 16β methyl-17,21 dipropionate) | $10^{-5}$ | 55 |
|  | $10^{-6}$ | 55 |
|  | $10^{-7}$ | 20 |
| difluoroasone | $10^{-5}$ | — |
| Diacetate (6,9 difluoro- 16 methyl diacetate) | $10^{-6}$ | — |
|  | $10^{-7}$ | 13 |
| Beclomethasone Dipropionate | $10^{-5}$ | — |
|  | $10^{-6}$ | — |
|  | $10^{-7}$ | 11 |

The 17,21 dipropionate of 6,9 difluoro prednisolone has been reported to be about twice as active in this assay as betamethasone-17 valerate [See Gardi et al Journal of Medicinal Chemistry 15,556 (1972)] which is generally accepted to be about 75% as active as beclomethasone dipropionate [See Harris, Journal of Steroid Biochemistry 6,711 (1975)]. Thus one can conclude that the 6,9 difloro-17,21 dipropionate is about 1.5 times as active as beclomethasone dipropionate. The results for compound 122 indicate that the compounds of this invention are by any standard potent vasoconstrictors. Also within the scope of the invention are pharmaceutical compositions for use in the treatment of inflammatory conditions comprising an effective amount of one or more of the novel compounds of the invention, together with a compatible pharmaceutically-acceptable carrier.

The pharmaceutical dosage forms are prepared according to procedures well known in the art and, where suitable, may contain other active ingredients e.g. antibiotics.

The following, non-limiting, examples illustrate topical formulations prepared in accordance with the invention:

| (a) Inhalation aerosol | |
|---|---|
| 6α-fluoro-9α-chloro-prednisolone 17,21-diester | 1–10 mg |
| oleic acid | 0.5 mg |
| trichlorofluoromethane | 3000 mg |
| dichlorofluoromethane | 7500 mg |
| (b) Lotion | |
| 6α-fluoro-9α-chloro-prednisolone 17,21-diester | 0.05–5.0 mg |
| ethyl alcohol | 400 mg |
| polyethylene glycol 400 | 300 mg |
| hydroxypropyl cellulose | 5 mg |
| propylene glycol | 300 mg |
| (c) Glycol ointment | |
| 6α-fluoro-9α-chloro-prednisolone 17,21-diester | 0.05–5.0 mg |
| hexylene glycol | 100 mg |
| propylene glycol monostearate | 20 mg |
| white wax | 60 mg |
| white petrolatum | 880 mg |

The processes described above are illustrated in the Examples below but should not be construed as limiting the invention, equivalents thereof and products produced thereby which will be obvious to one skilled in the art being considered as part of the invention.

PREPARATION 1

To a suspension of 100 g of 9β,11β-epoxy-16β-methyl-pregna-1,4-diene-17,21-diol-3,20-dione, prepared as described in Journal of the American Chemical Society, 82, 4012 (1960), in 800 ml of dry tetrahydrofuran and 150 ml of triethylorthopropionate at 20° was added 1 g of para-toluenesulphonic acid. After 1 hr the reaction mixture was neutralized with potassium acetate and diluted with water. The precipitate was collected, washed with water, and dried under vacuum to give in quantitative yield 9β,11β-epoxy-16β-methyl-pregna-1,4-diene-17,21-diol-3,20-dione 17,21-ethylorthopropionate. This latter compound was suspended in a mixture of 1 lt of methanol, 0.5 lt water and 5 ml glacial acetic acid and heated under reflux for 4 hr. The reaction mixture was then cooled to 20° and poured slowly into water (6 lt) under strong agitation. The resulting precipitate was collected, washed with water, and dried under vacuum to to give 9β,11β-epoxy-16β-methyl-pregna-1,4-diene-17,21-diol-3,20-dione 17-propionate (113 g), m.p. 150° (d), $[\alpha]_D + 47.5°$ (C=1, CHCl$_3$). This compound has not previously been described. In a similar manner, but instead of triethylorthopropionate using triethylorthoacetate, trimethylorthobutyrate, trimethylothovalerate, or trimethylorthobenzoate, there were obtained the 17-acetate, 17-butyrate, 17-valerate, and 17-benzoate, respectively, of 9β,11β-epoxy-16β-methylpregna-1,4-diene-17,21-diol-3,20-dione.

PREPARATION 2

To a solution of 113 g of 9β,11β-epoxy-16β-methyl-pregna-1,4-diene-17,21-diol-3,20-dione 17-propionate, prepared as described in Preparation 1, in 500 ml dry pyridine at 0° was added dropwise 75 ml of propionic anhydride and the mixture was allowed to stand at 20°-25° for 3 hr and then poured onto a mixture of ice/water/hydrochloric acid. The precipitate was collected, washed to neutrality with water, and dried under vacuum to give 122 g of 9β,11β-epoxy-16β-methyl-pregna-1,4-diene-17,21-diol-3,20-dione 17,21-dipropionate, m.p. 138°-140° C.

A sample crystallized from ethyl acetate-hexane had m.p. 148° C., $[\alpha]_D + 40°$ (C=1, CHCl$_3$).

In a similar manner, but using the appropriate acyl or aroyl chloride or anhydride together with the appropriate 17-ester of 9β,11β-epoxy-16β-methyl-pregna-1,4-diene-17,21-diol-3,20-dione, prepared as described in Preparation 1, there were obtained the 17,21-diacetate, 17-butyrate 21-acetate, 17-valerate 21-acetate, and 17-benzoate 21-acetate of 9β,11β-epoxy-16β-methyl-pregna-1,4-diene-17,21-diol-3,20-dione.

EXAMPLE 1

A mixture of 20 g of 9β,11β-epoxy-16β-methyl-pregna-1,4-diene-17,21-diol-3,20-dione 17,21-dipropionate, prepared as described in Preparation 2, and 2 g of para-toluenesulphonic acid in 200 ml of isopropenyl acetate was heated under reflux for 2 hr, neutralized with 20 g of potassium acetate, and evaporated to dryness under reduced pressure. The residue was dissolved in ethanol (200 ml) and treated at 0° for 16 hr with 10 g of perchloryl fluoride. The reaction mixture was then poured into 1 lt of iced water and the resulting precipitate was collected, washed thoroughly with water, and dried under vacuum to constant weight (22 g) to give 6α-fluoro-9β,11β-epoxy-16β-methyl-pregna-1,4-diene-17,21-diol-3,20-dione 17,21-dipropionate. A sample crystallized from methanol had the following characteristics: m.p. 210°

$[\alpha]_D$+47.5 (C=1, CHCl$_3$); $\gamma_{max}$ 1765, 1740, 1675, 1640, 1620, 1250–1225 cm$^{-1}$ $\lambda_{max}$ 245 nm ($\epsilon$16,500).

In a similar manner, but starting from the 17,21-diacetate 17-propionate 21-acetate, 17-butyrate 21-acetate, 17-valerate 21-acetate, and 17-benzoate 21-acetate diesters of 9β,11β-epoxy-16β-methyl-pregna-1,4-diene-17,21-diol-3,20-dione, prepared as described in Preparation 2, there were obtained the 17,21-diacetate, 17-propionate 21-acetate, 17-butyrate 21-acetate, 17-valerate 21-acetate, and 17-benzoate 21-acetate diesters, respectively, of 6β-fluoro-9β,11β-epoxy-16β-methyl-pregna-1,4-diene-17,21-diol-3,20-dione. (Table 2).

EXAMPLE 2

A mixture of 8 g of 6α-fluoro-9β,11β-epoxy-16β-methyl-pregna-1,4-diene-17,21-diol-3,20-dione 17,21-dipropionate, prepared as described in Example 1, and 16 g of lithium chloride in 160 ml glacial acetic acid was stirred at 20°–25° for 48 hr. The reaction mixture was poured into iced water and the precipitate was collected, washed well with water, and dried under vacuum to give in almost quantitative yield 6α-fluoro-9α-chloro-16β-methyl-prednisolone 17,21-dipropionate. After crystallization from ethyl acetate the product had the following characteristics: m.p. 231°–233°.

$\lambda_{max}$ 238 nm ($\epsilon$16,000); $[\alpha]_D$+85° (C=1, dioxane); $\gamma_{max}^{KBr}$ 3300, 1765, 1740, 1675, 1630, 1200 cm$^{-1}$.

In a similar manner, but starting from the 17,21-diacetate, 17-butyrate 21-acetate, 17-valerate 21-acetate, and 17-benzoate 21-acetate diesters of 6α-fluoro-9β,11β-epoxy-16β-methyl-pregna-1,4-diene-17,21-diol-3,20-dione, prepared as described in Example 1, there were obtained the 17,21-diacetate, 17-butyrate 21-acetate, 17-valerate 21-acetate, and 17-benzoate 21-acetate diesters, respectively, of 6α-fluoro-9α-chloro-16β-methyl-prednisolone (Table 3).

TABLE 2

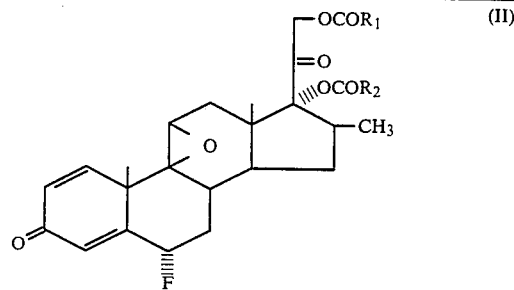

| $R_1$ | $R_2$ | | m.p. | $[\alpha]_D$ | (solvent) |
|---|---|---|---|---|---|
| C$_2$H$_5$ | C$_2$H$_5$ | β-CH$_3$ | 210° | +47.5° | (chloroform) |
| CH$_3$ | CH$_3$ | β-CH$_3$ | 229° (d) | +51° | (chloroform) |
| CH$_3$ | C$_2$H$_5$ | β-CH$_3$ | 150° | +43° | (chloroform) |
| CH$_3$ | C$_4$H$_9$ | β-CH$_3$ | 171° | +40° | (chloroform) |
| CH$_3$ | C$_6$H$_5$ | β-CH$_3$ | 239–240° | +33° | (chloroform) |

TABLE 3

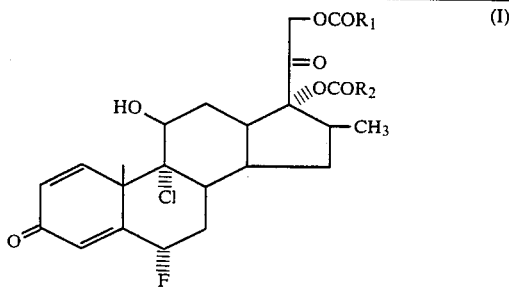

| $R_1$ | $R_2$ | p.f. | $[\alpha]_D$ |
|---|---|---|---|
| C$_2$H$_5$ | C$_2$H$_5$ | 231–233° | +85° |
| CH$_3$ | CH$_3$ | 240–243° | +81° |
| CH$_3$ | C$_2$H$_5$ | 217–219° | +84° |
| CH$_3$ | C$_4$H$_9$ | 181°](d.) | +89° |
| CH$_3$ | C$_6$H$_5$ | 267° | +86° |

What is claimed is:
1. A method of treating an inflammatory condition in a warm-blooded animal responsive to treatment with antiinflammatory agents, which comprises administering to said animal a nontoxic, antiinflammatory effective amount of 6-α-fluoro-9-α-chloro-prednisolone 17,21-diester of formula I

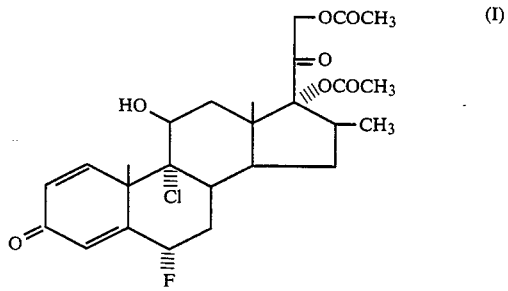

* * * * *